__United States Patent__ [19]

Wallshein

[11] 4,354,832
[45] Oct. 19, 1982

[54] ORTHODONTIC BIASSING DEVICE WITH DEFORMED SCREW THREADS

[76] Inventor: Melvin Wallshein, 8645 Bay Parkway, Brooklyn, N.Y. 11214

[21] Appl. No.: 149,304

[22] Filed: May 13, 1980

Related U.S. Application Data

[63] Continuation-in-part of Ser. No. 104,310, Dec. 17, 1979, which is a continuation-in-part of Ser. No. 785,587, Apr. 7, 1977, Pat. No. 4,200,979.

[51] Int. Cl.³ .............................................. A61C 3/00
[52] U.S. Cl. .......................................... 433/7; 254/98
[58] Field of Search .................... 433/7, 177; 254/204, 254/231, 85, 98, 100, 101, 102, 103, 232, 233, 234, 235, 236; 85/1 L, 47; 411/311, 310, 309, 308

[56] References Cited

U.S. PATENT DOCUMENTS

| | | | |
|---|---|---|---|
| 853,734 | 5/1907 | Reichert | 254/231 |
| 1,158,454 | 11/1915 | Camp | 85/1.2 |
| 1,928,402 | 9/1933 | Van Sickle | 254/98 |
| 2,177,004 | 10/1939 | Purtell | 411/311 |
| 2,504,291 | 4/1950 | Alderfer | 254/98 |
| 3,076,208 | 2/1963 | Moore | 411/311 |
| 3,104,493 | 9/1963 | Nalle | 254/98 |
| 3,134,290 | 5/1964 | Jentoft | 85/47 |
| 3,661,194 | 5/1972 | Macfarlane et al. | 411/311 |

FOREIGN PATENT DOCUMENTS

| | | | |
|---|---|---|---|
| 2722611 | 11/1978 | Fed. Rep. of Germany | 433/7 |
| 335798 | 3/1959 | Sweden | 433/7 |
| 651146 | 3/1979 | U.S.S.R. | 85/1.2 |

Primary Examiner—Gene Mancene
Assistant Examiner—John J. Wilson
Attorney, Agent, or Firm—Frishauf, Holtz, Goodman & Woodward

[57] ABSTRACT

An orthodontic biassing device with deformed screw threads on the elongated threaded member or receptacle member to provide an interference, but threadable, fit with its respective threaded member to substantially prevent backing-off of the screw due to reaction forces in the mouth of a patient. Sufficient play and tolerance is provided to enable the device to be relatively loose to facilitate alignment and installation in a patient's mouth. After installation, and under expansion conditions, the device tightens up to provide a substantially rigid structure.

4 Claims, 7 Drawing Figures

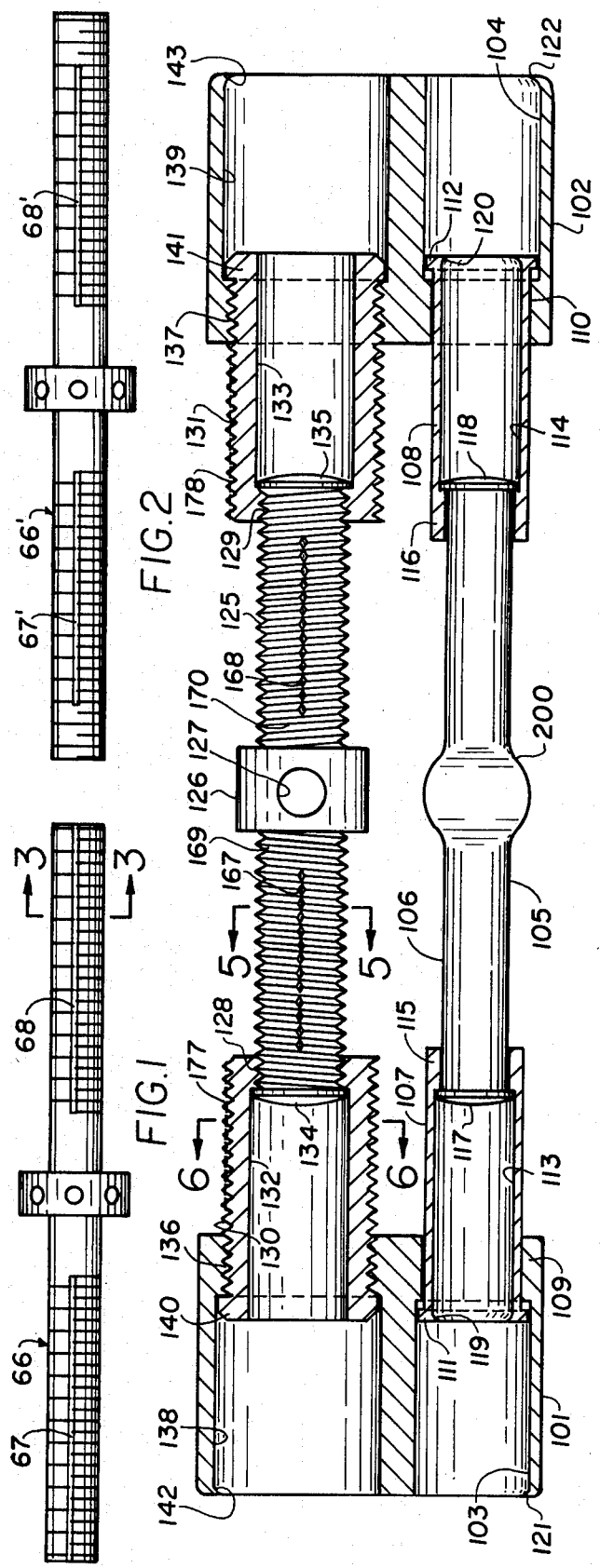
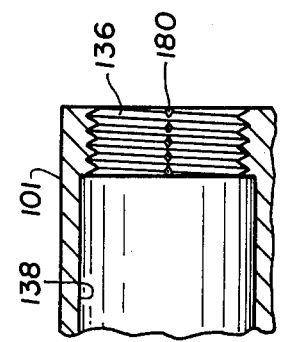
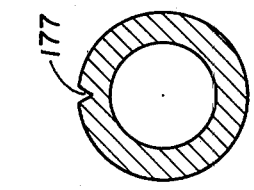
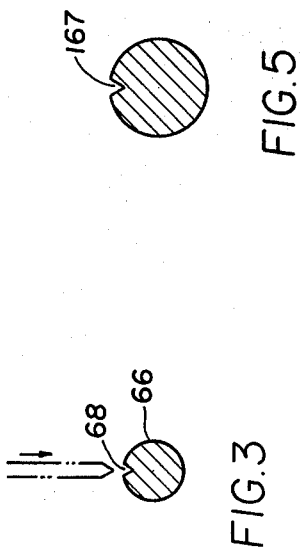

ORTHODONTIC BIASSING DEVICE WITH DEFORMED SCREW THREADS

CROSS-REFERENCE TO RELATED APPLICATIONS

1. This is a Continuation-In-Part of my prior application Ser. No. 104,310, filed Dec. 17, 1979, which in turn is a Continuation-In-Part of my prior application Ser. No. 785,587, filed Apr. 7, 1977, now U.S. Pat. No. 4,200,979.
2. U.S. Pat. No. 3,832,778.
3. U.S. Pat. No. 3,921,294.

BACKGROUND OF THE INVENTION

This invention relates to further improved orthodontic screw-type biassing devices, and more particularly to an improvement for preventing backing off of the screw which imparts biassing forces.

The object of the present invention is to provide an orthodontic biassing device, of the type which utilizes a screw for applying biassing forces, which substantially prevents or substantially reduces the screw back-off inherent in existing prior art devices.

It is a further object of the invention to provide an orthodontic biassing device, of the type which utilizes a screw for applying biassing forces, which has sufficient looseness and play to enable easy installation in the mouth, but which when after installation and under expansion conditions, provides a substantially rigid structure, as required.

BRIEF DESCRIPTION OF THE DRAWINGS

FIG. 1 is a front view of a typical actuator screw of a biassing device of the type to which the present invention pertains, incorporating the backing-off preventing means of the present invention;

FIG. 2 is a modified embodiment of FIG. 1;

FIG. 3 is a cross-sectional view of the screw of FIG. 1 taken along the line 3—3 in FIG. 1;

FIG. 4 illustrates an orthodontic biassing device embodying the present invention;

FIGS. 5 and 6 are cross-sectional views taken along the line 5—5 and 6—6, respectively, in FIG. 4; and FIG. 7 is a partial sectional view of another embodiment of the invention.

DETAILED DESCRIPTION

The entire contents of my prior applications Ser. Nos. 785,587, filed Apr. 7, 1977 and 104,310, filed Dec. 17, 1979, are incorporated herein by reference.

FIG. 1 illustrates an actuator screw, which may replace the screw 10 of the device illustrated in FIG. 2 of Ser. No. 785,587, filed Apr. 7, 1977, or which may replace the screw 5 or other similar screws shown in various Figures in my Ser. No. 104,310, filed Dec. 17, 1979. A detailed discussion of the environment in which the screw of FIG. 1 may be located is not given since the entire contents of said prior applications are incorporated herein by reference.

The screw 66 shown in FIG. 1 has the crest and a portion of the threads between the crest and root altered or deformed substantially along lines 67, 68 by means of, for example, impacting the screw by an elongated anvil (not shown). The anvil may be preferably V-shaped with a sharp or a relatively blunt leading edge, the leading edge of the V-shaped being impacted on the screw threads to produce deformation of the screw threads along lines 67, 68.

FIG. 2 illustrates a modified form wherein the screw threads of the screw 66' are not deformed along the complete length thereof. The remote end portions of the screw are not deformed in this embodiment. In many instances, it is desired to first assemble the orthodontic biassing device, such as those shown in my prior co-pending applications mentioned above, or in FIG. 4 hereof, run out the screws to the maximum extent, then deform the screws as shown in FIG. 2 by impacting same with an anvil, or the like, and then retract the screws into the respective body members or body housings to retract the biassing device to its minimum expanded state. The reason for this is that if the screw threads are deformed as shown in FIG. 1 or FIG. 2 before assembly of the device, assembly becomes more difficult. It has been found advantageous to deform the threads after assembly of the device by the method described above.

FIG. 3 is a sectional view of the embodiment of FIG. 1, the sectional view of the embodiment of FIG. 2 taken in the same place being identical. A typical deformation of the threads due to impacting by an anvil (shown in dashed lines) is shown in FIG. 3. Other deformations could be used, as desired. Moreover, instead of producing a straight line deformation 67, 68, the deformation could be made in elongated adjacent segments so that the result approaches the straight line deformation. Moreover, more than one deformation, such as line of deformation 67, 68, could be applied around the circumference of the screw.

FIG. 4 illustrates an orthodontic biassing device according to the present invention in its assembled state. In this embodiment, the screw 125 is deformed along lines 167, 168, as shown in FIG. 1, for example by means of impacting with an anvil or the like. The screw threads on the end threaded members 130, 131 are also deformed, as illustrated by 177, 178, also for example by means of an anvil impacting the threads. As seen in FIG. 4, screw material from the crest areas of the deformed portions of the threads is located in the groove areas of the threads. The deformation is sufficient so that the screws may still be threaded to expand the device, against the resistance of the deformed threaded portions, by means of a tool inserted in the opening 127 of spindle 126. However, the resistance imparted by the engagement of the deformed threads with the internally threaded mating portions, substantially prevents backing off of the screw due to reaction forces applied to the body housings 101, 102.

FIGS. 5 and 6 illustrate typical deformation of the threads of the screw members 125 and 130, 131. As mentioned above with respect to FIG. 3, the type of deformation illustrated in FIG. 5 and FIG. 6 is exemplary. Other types of deformations may be provided, for example in segments, dots or dimples, more than one line of deformation about the circumference of the screws, etc. The critical feature is to provide sufficient resistance to prevent backing-off due to reaction forces, but still permitting actuation of the device by rotation of the screws by means of a tool inserted in the openings of spindle 126. The anvil end may be blunt, flat, sharp, etc.

FIG. 7 is a partial sectional view of one of the body members 101. The threaded bore 136 thereof has its threads deformed along the axis of the bore as generally indicated at 180 in FIG. 7. The deformation 180 can be produced by means of a blunt or sharp instrument, such as shown in FIG. 3, or by any other type of impacting instrument to deform the threads. The threads need not be deformed in a V-shape, but may be deformed in any manner so as to provide the interference fit which also permits threadable engagement of the bore 136 with its associated threaded member. The threaded bore 128 of intermediate member 130 can also be deformed substantially as shown in FIG. 7, as may be the bores of intermediate member 131 and body member 102.

It should also be clear that only one side of the threaded member need be deformed, depending upon the amount of deformation and interference fit desired. Likewise, only one threaded bore on each side of the screw member 125 need be deformed, if desired. The deformations can be provided in any or all of the members, in any combination whatsoever, to provide the desired interference, but threadable, fit.

The mating threads and the clearances between the guide bars and the various housings and receptacles, is such that when the device is in its minimum expanded state (that is, bodies 101, 102 in their closest-together positions), the device has a significant amount of play or looseness so that it can be readily aligned and mounted to teeth of a patient. It has been found that when the device is extremely rigid in its contracted or minimum-expanded state, it is difficult to install. By virtue of the present invention, the device is loose when in its minimum-expanded state to facilitate alignment and installation in a patient's mouth. When installed, the body members 101, 102 are firmly attached to respective teeth. During expansion, the teeth tilt outwardly, which results in the tilting of the body members 101, 102 and tightening up of the system to make it substantially rigid. Further, as the screws are screwed outwardly to expand the biassing device against reaction forces in the mouth of a patient, the elements "tighten up" and provide an even more rigid structure.

The deformed threaded portions 167, 168, 177, 178 serve to more tightly engage the respective mating threaded receptacles so as to enhance "tightening up" of the device during the expansion stage.

It has further been found advantageous to provide an un-deformed area of the screw threads in the vicinity where the screw threads are engaged with the threads of their respective receptacles when the biassing device is in its collapsed or minimum expanded state. This non-deformed section of the screw threads is shown, for example, by the reference numerals 169, 170 in FIG. 4. Similarly, the innermost ends of end members 130, 131 may not be deformed. This provides more looseness or play between parts when the device is in its contracted condition than when it is in its expanded condition.

As mentioned above, it is preferable to first assemble the biassing device, for example to the condition shown in FIG. 4, and to then impact the threads with, for example, an anvil, to deform the exposed threaded portions, and to then back off the screws to contract the device to the size for installation in the mouth of a patient. The deformation of the threads is such that an interference, but threadable, fit is achieved, the interference or friction being sufficient to substantially prevent backing off of the screw due to reaction forces applied to the device which would otherwise tend to cause the screw to thread back into the body members.

I claim:

1. A method of fabricating an orthodontic biassing device comprising at least first and second body members having oppositely threaded bores therein, and an elongated threaded member having end portions which are oppositely threaded, said elongated threaded member being threadably engaged in said threaded bores of said body members, the method comprising:
    assembling the biassing device by threadably engaging said elongated threaded member into said first and second body members;
    unthreading said elongated threaded member from said first and second body members to cause said first and second body members to separate from each other and to thereby expose at least a portion of the threaded end portions of said elongated threaded member; and
    impacting at least a portion of the exposed threaded portions of said elongated threaded member to deform threads thereof so as to provide an interference, but threadable, fit of said elongated threaded member in the respective threaded bores of said body members when it is threaded back into said body members.

2. The method of claim 1, wherein said impacting step comprises impacting at least a portion of said exposed threads with a generally V-shaped impact member.

3. The method of claim 1 or 2 wherein said elongated threaded member is a telescoping threaded member having inner and outer threaded members, and impacting at least a portion of the exposed threaded portions of said inner and outer threaded members to deform threads thereof so as to provide an interference, but threadable, fit of said inner and outer elongated threaded members in the respective threaded bores into which they engage.

4. The method of claim 1, wherein said step of impacting deforms said threads such that portions between the crests and roots of the deformed threads are located into the adjacent grooves of the threads in the deformed areas to thereby provide said interference, but threadably fit.

* * * * *